United States Patent
Al-Labban

(10) Patent No.: US 6,224,574 B1
(45) Date of Patent: May 1, 2001

(54) COMBINED SCALPEL AND SYRINGE DEVICE

(76) Inventor: Hassan Al-Labban, 71 Ackerman Ave., Suite 282, Clifton, NJ (US) 07011

( * ) Notice: Subject to any disclaimer, the term of this patent is extended or adjusted under 35 U.S.C. 154(b) by 0 days.

(21) Appl. No.: 09/421,342

(22) Filed: Oct. 18, 1999

(51) Int. Cl.[7] .................................................. A61M 5/00
(52) U.S. Cl. ............................................ 604/187; 606/167
(58) Field of Search ........................... 604/187, 22, 218; 606/167

(56) References Cited

U.S. PATENT DOCUMENTS

| | | | |
|---|---|---|---|
| 2,656,600 | 10/1953 | Barbee | 30/123 |
| 3,990,453 | 11/1976 | Douvas et al. | 128/305 |
| 4,642,090 | * 2/1987 | Utrata | 604/22 |
| 4,960,419 | * 10/1990 | Rosenberg | 606/167 X |
| 5,088,198 | 2/1992 | Drusiani | 30/123.3 |
| 5,161,308 | 11/1992 | Hayward | 30/123.3 |

* cited by examiner

Primary Examiner—John D. Yasko
(74) Attorney, Agent, or Firm—Henderson & Sturm LLP

(57) ABSTRACT

A combined scalpel and syringe device 10 for dispensing fluid medicants at an incision site wherein the device 10 includes a hollow handle member 20 dimensioned to receive a plunger member 40 for forcing fluid from the interior of the handle member 20 through a discrete aperture 23 formed on one end 22 of the handle member 20 which is further provided with a scalpel member 30 and a syringe needle member 50 which communicates with the discrete aperture 23.

2 Claims, 1 Drawing Sheet

COMBINED SCALPEL AND SYRINGE DEVICE

BACKGROUND OF THE INVENTION

1. Field of the Invention

The present invention relates to the field of surgical implements in general, and in particular to a surgical scalpel which is provided with a manually actuated syringe feature.

2. Description of Related Art

As can be seen by reference to the following U.S. Pat. Nos. 2,656,600; 3,990,453; 4,642,090; 5,088,198; and 5,161,308, the prior art is replete with myriad and diverse combined devices used for a variety of tasks.

While all of the aforementioned prior art constructions are more than adequate for the basic purpose and function for which they have been specifically designed, they are uniformly deficient with respect to their failure to provide a simple, efficient, and practical device for providing a manually controlled flow of liquid such as distilled water or medicinal fluid to an incision site.

As most surgeons are aware, there are certain instances during surgical procedures wherein it is desirable to introduce liquid into a incision site to either flush the opening of debris or to directly apply a dose of liquified medicine at the incision site, and to prevent the development of surgical wound infections which are considered to be the second most common hospital acquired infections which contribute significantly to morbidity and mortality, as well as excess costs for hospitalized patients.

As a consequence of the foregoing situation, there has existed a longstanding need for a new and improved hand held surgical implement that combines a syringe or quasi-syringe with a scalpel blade, and the provision of such a construction is a stated objective of the present invention.

BRIEF SUMMARY OF THE INVENTION

Briefly stated, the combined scalpel and syringe device that forms the basis of the present invention comprises in general, a handle unit, a scalpel unit, and a syringe unit wherein at least a portion of the syringe unit is contained within the handle unit.

As will be explained in greater detail further on in the specification, the handle unit includes a generally hollow cylindrical handle member having an open end and a substantially closed end provided with a discrete aperture.

The scalpel unit includes a scalpel blade member fixedly secured to the substantially closed end of the handle member such that the handle member can be manipulated in the normal fashion to function as a scalpel device.

In addition, in the preferred embodiment of the invention, the syringe unit comprises a syringe needle member operatively connected to the discrete aperture in the substantially closed end of the handle member and a plunger member slidably disposed within the hollow handle member to force fluid from the handle member through the syringe member. The syringe member is aligned parallel to the upper flat edge of the scalpel member.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
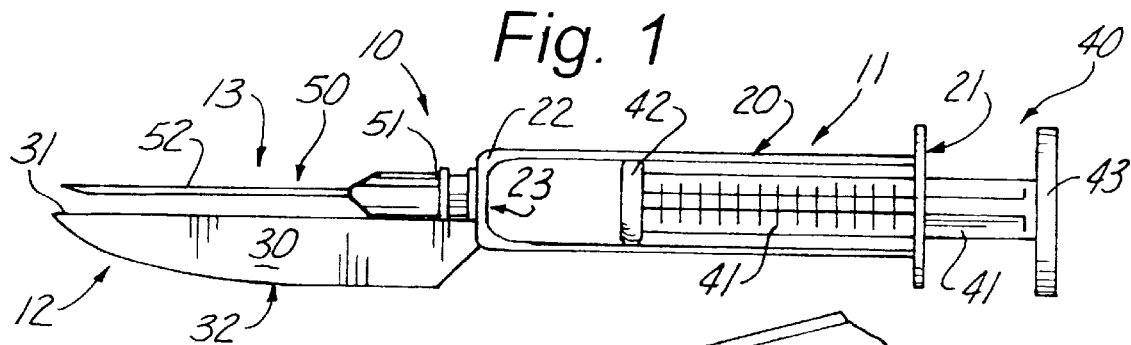
FIG. 1 is a side elevation view of the preferred embodiment of the combined scalpel and syringe device of this invention.

As can be seen by reference to the drawings, and in particular to FIG. 1, the combined scalpel and syringe device that forms the basis of the present invention is designated generally by the reference number 10. The device 10 comprises in general, a handle unit 11, a scalpel unit 12, and a syringe unit 13. These units will now be described in seriatim fashion.

In the preferred embodiment of this invention depicted in FIGS. 1 and 2, it can be seen that the handle unit 11 comprises an elongated generally cylindrical hollow handle member 20 having an open inboard end 21 and a substantially closed outboard end 22 provided with a discrete aperture 23 whose purpose and function will be described presently.

In addition, the scalpel unit includes an elongated scalpel blade member 30 having a flat upper surface 31 and a tapered lower cutting surface 32. The inboard end of the scalpel blade member 30 is fixedly secured to the outboard end 22 of the handle member 20.

Figure 2:
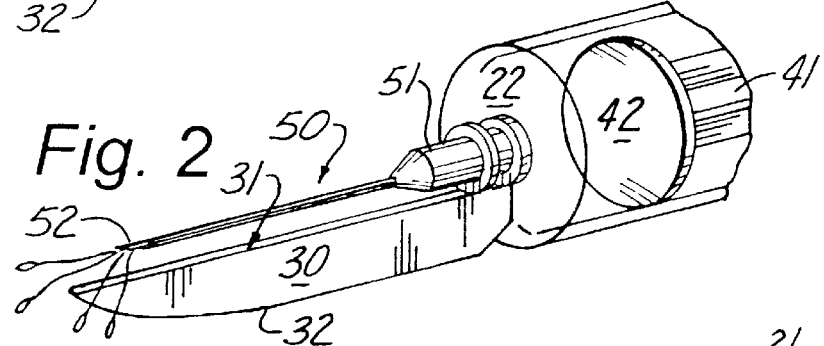
FIG. 2 is an isolated detail view of the outboard end of the preferred embodiment.

Still referring to FIGS. 1 and 2, it can be seen that the syringe unit 13 comprises a plunger member 40 which includes a plunger shaft 41 having a plunger head 42 disposed on one end and an enlarged plunger actuator 43 disposed on the other end. The plunger head 42 is adapted to sealingly engage the interior walls of the handle member 20 as the plunger member 40 forces fluid through the discrete aperture 23 in the handle member 20 in a well recognized fashion.

Furthermore, the syringe unit 13 also includes a conventional syringe needle member 50. The needle base element 51 is fixedly secured to the outboard end 22 of the handle member 20 such that the hollow needle element 52 is in open fluid communication with the discrete fluid aperture 23 in the handle member 20.

Figure 3:
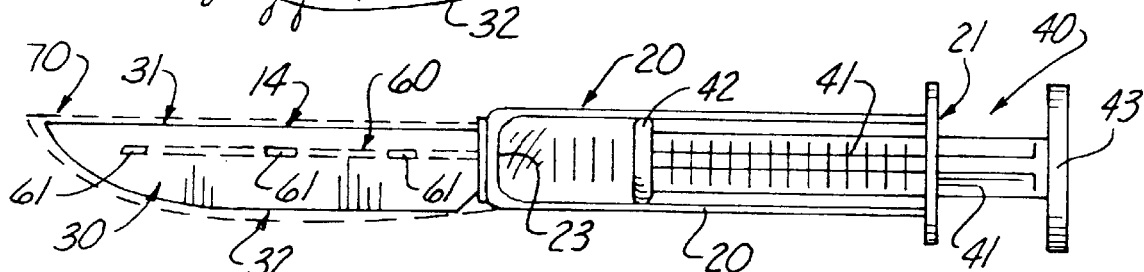
FIG. 3 is a side elevational view of an alternate version of the preferred embodiment.
Figure 4:
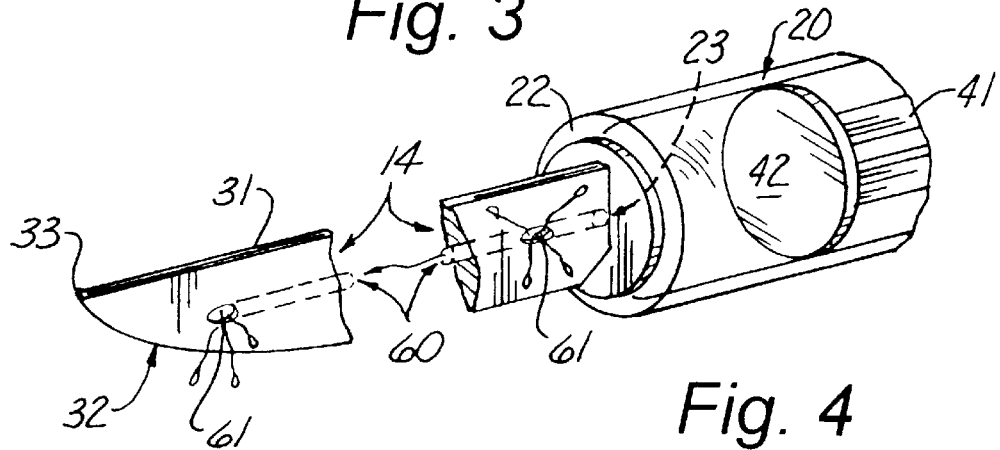
FIG. 4 is an isolated cut away detail view of the outboard end of the alternate version of the preferred embodiment.

Turning now to FIGS. 3 and 4, it can be seen that in the alternate version of the preferred embodiment, the handle member 20 and the plunger member 40 are virtually identical to the equivalent structures shown in FIGS. 1 and 2. However, in this version, a hybrid scalpel/syringe unit 14 is employed wherein the scalpel member 30 is provided with an elongated narrow syringe passageway 60 which extends from a point proximate the tip 33 of the scalpel member 30 to the inboard end of the scalpel member 30. The syringe passageway 60 is aligned with the discrete fluid aperture 23 in the hollow handle member 20.

In addition, the syringe passageway 60 is further provided with a plurality of fluid outlet ports 61 which allow fluid to be dispensed at various locations along the length of the scalpel blade member 30.

Furthermore, as indicated in FIG. 3, this invention also contemplates the provision of a cover member 70 shown in phantom which conforms tot he outboard end of the device 10 to prevent accidental punctures in a well recognized fashion.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A combined scalpel and syringe device comprising:

an elongated hollow handle member having an open end and a substantially closed end provided with a discrete fluid aperture;

a scalpel blade member fixedly secured to the substantially closed end of the handle member wherein said scalpel blade member has a lower narrow cutting surface and an upper generally flat surface; and, means associated with the discrete fluid aperture for delivering fluid from the interior of the hollow handle member to a portion of the scalpel blade member, wherein said means comprises:

a plunger member at least partially disposed within the hollow handle member and including a plunger shaft having one end provided with a plunger head and having the other end provided with a plunger actuator; and, a syringe needle member having a hollow base element disposed in open fluid communication with the interior of the hollow base element wherein the base element is further provided with a hollow needle element.

2. The device as in claim 1 wherein said hollow needle element is disposed generally parallel to the upper surface of the blade member.

* * * * *